(12) United States Patent
Lefebvre (10) Patent No.: US 7,657,070 B2
(45) Date of Patent: Feb. 2, 2010

(54) AUTOMATED SYSTEM OF PROCESSING BIOLOGICAL SPECIMENS AND METHOD

(75) Inventor: Gilles Lefebvre, Torrance, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 711 days.

(21) Appl. No.: 11/336,468

(22) Filed: Jan. 20, 2006

(65) Prior Publication Data

US 2007/0172100 A1 Jul. 26, 2007

(51) Int. Cl.
*G06K 9/00* (2006.01)

(52) U.S. Cl. ............... 382/128; 382/129; 382/133; 382/181; 382/209; 382/217

(58) Field of Classification Search ........... 382/128, 382/133, 134, 181
See application file for complete search history.

(56) References Cited

U.S. PATENT DOCUMENTS

| | | | | |
|---|---|---|---|---|
| 4,761,075 | A * | 8/1988 | Matsushita et al. | 356/39 |
| 5,733,721 | A * | 3/1998 | Hemstreet et al. | 435/6 |
| 5,933,519 | A * | 8/1999 | Lee et al. | 382/133 |
| 6,032,678 | A * | 3/2000 | Rottem | 600/437 |
| 7,050,620 | B2 * | 5/2006 | Heckman | 382/133 |
| 7,346,200 | B1 * | 3/2008 | Tsipouras et al. | 382/128 |
| 7,346,205 | B2 * | 3/2008 | Walker, Jr. | 382/133 |
| 2003/0228038 | A1 * | 12/2003 | Douglass et al. | 382/128 |
| 2004/0253662 | A1 | 12/2004 | Heid et al. | |
| 2005/0144044 | A1 | 6/2005 | Godschall et al. | |
| 2005/0159982 | A1 | 7/2005 | Showalter et al. | |
| 2005/0235542 | A1 | 10/2005 | Metzner et al. | |
| 2006/0210432 | A1 | 9/2006 | Victor et al. | |

FOREIGN PATENT DOCUMENTS

| | | |
|---|---|---|
| WO | WO 01/37192 | 5/2001 |
| WO | WO 03/045560 | 6/2003 |
| WO | WO 2004/059288 | 7/2004 |
| WO | WO 2004/074845 | 9/2004 |
| WO | WO 2004/099937 | 11/2004 |
| WO | WO 2007/078842 | 7/2007 |

OTHER PUBLICATIONS

European Search Report for EP Appln No. 07100808.0, mailed Dec. 27, 2007 (8 pages).
"Absolute Intelligence," http://www.sakura-americas.com/products/DRS.html, Jun. 29, 2005.

(Continued)

*Primary Examiner*—Tom Y Lu
(74) *Attorney, Agent, or Firm*—Blakely Sokoloff Taylor & Zafman LLP (57) ABSTRACT

An automated laboratory slide management and interpretation system and method in which slides are stained and then digitally imaged and the images are interpreted prior to referral to a diagnostician or placement in storage. The interpretation of the images involves the application of pattern recognition principles to compare the digitized images to known sample patterns from a variety of sources. Additionally, based on the results of the interpretation, the slide may undergo additional testing or staining, and additional samples may be prepared and tested. The specimens may be delivered to the diagnostician along with a tentative diagnosis.

13 Claims, 7 Drawing Sheets

OTHER PUBLICATIONS

"Fast coverslipping; quality results," http://www.sakura-americas.com/products/sca.html, Jun. 29, 2005.

"Creating new horizons in productivity," http://www.sakura-americas.com/products/xpress.html, Jun. 29, 2005.

"Discover the unique union of staining and coverslipping," http://www.sakura-americas.com/products/prismafilm_1.html, Jun. 29, 2005.

"Training and Workshops," http://www.biogenex.com/rpfile.php?pagename=workshops, Dec. 22, 2005.

Gombrich, Eric, et al., "Toward an automated paradigm for cancer screening," IVD Technology, Nov./Dec. 2001 (10 pages).

"Our Products," http://www.sysmex.com/usa/ourproducts/our_products_detail.cfm?p_id=33, Dec. 22, 2005.

"Sysmex Releases the World's First Automated Hemotology Slide Preparation Unit with Web Camera," http://www.sysmex.co.jp/en/news/press /2004/040909.html, Sep. 9, 2004 (3 pages).

Anderson, Ross, "Haematology Completely Automated Using an Innovative Dual HST Transportation System, Meru Work Area manager and Molis Software," Sysmex J. Int., 2003, pp. 48-52, vol. 13, No. 1.

"Automation Systems manage hematology testing processes," Thomas Publishing Company, Nov. 15, 2005 (4 pages).

* cited by examiner

AUTOMATED SYSTEM OF PROCESSING BIOLOGICAL SPECIMENS AND METHOD

FIELD OF THE INVENTION

The present invention relates to a system of processing and examining biological specimens in a laboratory environment.

BACKGROUND OF THE INVENTION

In various settings, examination of biological specimens is required for diagnostic purposes. Generally speaking, pathologists and other diagnosticians collect and study samples from patients, and utilize microscopic examination, and other devices to assess the samples at cellular levels. Numerous steps typically are involved in pathology and other diagnostic process, including the collection of biological samples such a blood and tissue, processing the samples, preparation of microscope slides, staining, examination, re-testing or re-staining, collecting additional samples, re-examination of the samples, and ultimately the offering of diagnostic findings. Numerous medical or veterinary personnel may be involved in the diagnostic processes, including surgeons, phlebotomists or other operating personnel collecting samples, pathologist, histologists and other personnel processing, transporting and examining the samples and so on. The complexity of the tissue handling procedures from operating theatre to laboratory and back to diagnosticians or surgeons have become increasingly complex in large medical environments where high volumes of samples need to be handled, processed and examined on a daily basis.

Various steps of the tissue handling procedures have been automated using instruments each of which typically are controlled by a dedicated computer or an on-board computerized controller. In some laboratories, information can be shared between automated instruments and/or a networked laboratory or hospital information system, such as to store patient or tracking data. One example of an automated instrument is an automated tissue processing system in which biological samples are fixed and infiltrated with paraffin in an automated fashion. Such a tissue processing systems are the TISSUE-TEK® VIP™ and the TISSUE-TEK® XPRESS® processing systems available from Sakura Finetek U.S.A., Inc. of Torrance, Calif.

Another example of automation is an automated microscope slide coverslipper, which applies coverslips to microscope slides in an automated fashion. An example of such an automated coverslipper is the TISSUE-TEK® SCA™ coverslipper available from Sakura Finetek U.S.A., Inc. of Torrance, Calif. A further example of automation in laboratories is an automated microscope slide stainer, in which various stains, other reagents and washes are automatically applied to batches of microscope slides. An example of such an automated slide stainer is the TISSUE-TEK® DRS™ stainer system available from Sakura Finetek U.S.A., Inc. of Torrance, Calif.

Despite the assistance of automated instruments, pathologists, other diagnosticians and laboratory personnel typically must be involved in numerous steps during the processing and examination of biological samples. For example, once a sample has been stained, the sectioned stained sample on a microscope slide typically is physically examined under a microscope. This typically involves transport of the microscope slide to a diagnostician who is located outside the laboratory, or in other cases may involve a diagnostician going to the laboratory to examine the microscope slide. Following this initial examination step, the diagnostician evaluates whether additional testing is required. Such additional testing might involve collecting further samples from a patient, or further testing of samples already collected. For example, the diagnostician may require that the existing sample be sectioned further and a different staining regimen or other protocol be applied. This can result in iterations of one or more of collection, grossing, processing, infiltration, embedding, sectioning, coverslipping, staining, examination etc. All of this can result in time delays, as well as tissue impairment. Following the iterations of additional tests and procedures, the pathologist repeats the examination process, and may then request still further tests in an iterative fashion until an ultimate finding is reached. Even with automated instruments in these processes, there are numerous transport, and human interventions required.

Accordingly, there is a need for a system and method of biological specimen processing and examination that increases automation and accuracy involved in automation, reduces the amount of transport of processed specimens in the examination process, and reduces lag times, inconvenience and potential for degradation involved in iterative diagnostic and processing steps. Moreover there is a need for increased speed in these processes to enhance diagnosis and treatment.

SUMMARY OF THE INVENTION

The present invention alleviates to a great extent the disadvantages of the known systems and methods of automated biological specimen processing and examination by providing an automated system in which biological specimens are processed with feedback data provided via networked communications, and wherein diagnostic image data is created and delivered to desired people, such as diagnosticians, and further instructions can be generated for iterative processing and review, without the necessity of individual slide review, if desired.

In the present system, an automated processing apparatus is provided to collect and process biological samples, take images of the microscope data, deliver the images as desired for review and then determine further processing steps. In one example, a specimen is collected and then processed as desired in order to generate stained microscope slides. This includes automated tissue processing including paraffin infiltration, with data recorded in a hospital or laboratory information system. The processed specimen is passed on for embedding as desired, either in the same automated machine or in another one. Again, data is optionally generated and recorded. The embedded specimen may then be passed on for sectioning, with data again optionally generated and recorded. The sections are positioned on microscope slides as desired, coverslipped and optionally de-paraffinized, washed and stained in any desired order with data again optionally generated and recorded at any desired times in these automated processes. The completed microscope slides are imaged under microscopic examination, such as by using a digital camera incorporating a charge-coupled device (CCD) imager, and the image data is stored and delivered as desired. In one embodiment, the image data is passed on to an interpretation module, such as a pattern recognition system, which generates a preliminary diagnosis such as based on comparison with a pattern database or pattern determination protocol (s). Generation of additional microscope slides can be instructed automatically depending on the determination of the interpretation system (such as additional staining, or additional sectioning, staining coverslipping, or additional sample gathering, processing, embedding, sectioning, coverslipping etc.). Then additional images are created and examined using the pattern recognition module as desired, and any additional processing may be requested.

In addition, a diagnostician, such as a surgeon or pathologist, may access the image data and the interpretation module reports at any point during or at the end of this process, to request additional diagnosis activity or to instruct the automated system as desired. In one example, the diagnostician orders that additional sectioning and staining protocols be performed. In addition, based on the image data or pattern recognition reports, the diagnostician may request delivery of one or more microscope slides for personal inspection. Alternatively, the system may automatically position one or more microscope slides in a designated area for delivery to the diagnostician, or the system may make the slides available in any other fashion, whereby examination by a diagnostician can be performed.

In one embodiment, a "Reflex Staining" procedure is implemented. In that procedure, the system recommends specific staining and/or testing of biological samples based on pattern recognition reports of reports of an interpretation module.

In another aspect of the invention, the movement of both information and biological samples are provided. For example, biological samples proceed through processing, embedding, microtomy, staining and optional coverslipping systems, and to an imager. Following imaging, the sample may undergo further sectioning, staining etc. prior to being sent to a pathologist or storage. The information generated in the material processing devices can be accessed and otherwise shared by other devices and computers, including the interpretation module, information systems, and diagnostician work station, among others.

In another aspect of the invention, image data may be transmitted through an information path (such as a network or plural networks) to an interpretation module, which communicates with one or more databases and conducts pattern recognition to assist in the automated interpretation. Once the interpretation has generated results, the system may then route the material to undergo additional testing, request additional material to be tested, or route the material to a diagnostician or storage facility. In one example, the diagnostician may be notified that results are available for their consideration by electronic notification, such as by an e-mail, computer screen pop-up announcement, banner announcement, pager message or automated phone call. The diagnostician may consider the image data, the interpretation report, and/or other data, and may agree with the interpretation, disagree, provide other diagnosis, or order additional procedures. The diagnostician or a technician also can optionally intervene and override recommendations of additional procedures by the interpretation module.

The system may route samples in various ways. For example, the sample may be interpreted as normal and routed to the diagnostician. The sample may alternatively be interpreted as abnormal or diseased and routed to the diagnostician with a preliminary finding. The sample could also be interpreted as abnormal with no identified finding or recommendation and therefore sent to the diagnostician for assessment.

The interpretation module can access any desired data in order to formulate its report, in addition to the image data provided by the imaging system. For example, the interpretation module may consider the patient's records to determine prior conditions and known risk factors related to various ailments. Likewise, other images within the information system can be compared and contrasted to achieve multiple purposes, such as assessing the progression of a disease. Based on the information acquired in this process, the system can monitor a particular patient's ongoing condition, or it can be used on a broader scale to assess epidemiological information on a large number of individuals.

In one summary aspect of the invention, a system of processing biological specimens is provided including a biological material handling system, a communication infrastructure in communication with the material handling system, slide imaging module and an interpretation module in communication with the slide imaging module utilizing the slide image data in order to generate an initial interpretation of the image data. The slide imaging module is in communication with the interpretation module either via a direct data link (wireless or wired), via the communications infrastructure or both. In other aspects of the invention a determination module generating staining instruction data and/or a slide staining module carrying out at least one staining procedure and receiving said staining instruction data, and/or a sectioning device, and/or a sectioning instruction receiving module, and/or a coverslipper module, and/or other material handling or processing components suitable for generating material image data and transferring it to either an automated system and/or human for viewing and interpretation.

These and other features and advantages of the present invention will be appreciated from review of the following detailed description of the invention, along with the accompanying figures in which like reference numerals refer to like parts throughout.

DETAILED DESCRIPTION OF THE INVENTION

In the following paragraphs, the present invention will be described in detail by way of example with reference to the accompanying drawings. Throughout this description, the preferred embodiments and examples shown should be considered as exemplars, rather than as limitations on the present invention. As used herein, the "present invention" refers to any one of the embodiments of the invention described herein, and any equivalents. Furthermore, reference to various aspects of the invention throughout this document does not mean that all claimed embodiments or methods must include the referenced aspects.

Figure 1:
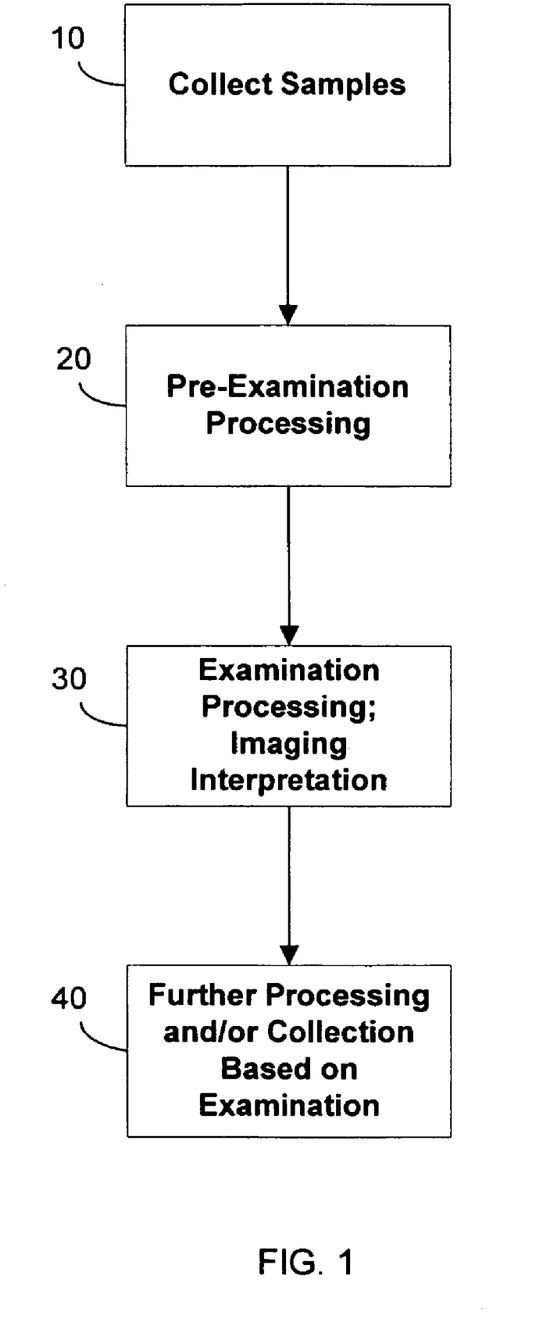
FIG. 1 is a block illustration of an overview of steps performed in an automated system of processing and examining biological specimens in accordance with the present invention.

In overview, the system of the present invention involves apparatuses and systems for performing a series of operations including tissue collection, processing, examination and iterative processing or collection as shown in FIG. 1. As illustrated in box 10, a biological sample is collected, such as via a biopsy or drawing blood. The biological sample is conveyed to a material handling system, whether manual transport, via cart or automated transport. In a hospital embodiment, the specimen may be delivered to a medical laboratory, whether on-site or at a remote location. A specimen, or group of specimens, is processed into a condition suitable for desired examination, as illustrated with box 20.

There are numerous possibilities for processing the sample for such examination. For example, a blood sample might be drawn and a small amount positioned on a microscope slide and coverslipped, such as done in a hematology laboratory. Optional staining or other testing protocol may then be performed. In the embodiments illustrated in FIGS. 2-5, a tissue sample may be processed into a condition suitable for examination, such as for example being infiltrated and embedded with paraffin, sectioned, stained/tested, positioned on a microscope slide, and coverslipped. Generally speaking, the system provides for the processing of a biological sample sufficiently to enable imaging in an imaging module, and examination of image data and/or the sample by a diagnostician. It should be noted that, as used herein, "diagnostician" refers to any person who may wish to view image data, such as pathologists, surgeons, nurses, researchers, technicians and administrators.

After a sample, or group of samples, is prepared for examination, it may be examined and the data may be made available to a diagnostician and/or an interpretation module, as illustrated with box 30. In an embodiment, the examination is conducted optically such as via microscope, but other forms of examination may also be performed. Image data may be created, such as using a digital imager including CCD technology. The image data preferably is made available for access by a diagnostician if desired, and optionally the diagnostician is notified such as by electronic notification, such as by an e-mail, computer screen pop-up announcement, banner announcement, pager message or automated phone call. In a preferred embodiment, the image data may also be accessed, or otherwise made available, to an interpretation module. The interpretation module conducts digital processing, such as by using pattern recognition technology in order to develop a preliminary diagnosis, and generates instructions or recommendations for additional processing. The additional processing, illustrated with box 40, may include collecting additional biological samples, or further processing samples already collected such as running additional or different test procedures or staining protocols (as illustrated in boxes 10 and 20). Then examination, imaging and interpretation of the sample may be continued until the system or diagnostician deems it to be complete. These repeated tests and examinations are referred to herein as iterative processing, testing or examination. In another aspect of the invention, the diagnostician may access reports that are based on the comparison data created by the interpretation module. In a further aspect of the invention, the diagnostician may order or conduct further iterative processing, testing or examination.

FIGS. 2-5 illustrate examples of automated systems for processing and examining biological specimens in accordance with the present invention. In these figures, information pathways are illustrated with solid lines and/or arrows and material pathways are illustrated with double lines and outlined arrows. As used herein, "material" refers to any biological material including histological and cytological specimens that may be examined in a medical, autopsy, veterinary or research laboratory procedure. The biological material may include tissue samples or specimens, and/or biological fluids such as blood, plasma, etc. Although the illustrated examples are described in relation to tissue, the described systems are not so limited. As used herein the biological material will be referred to interchangeably as a specimen, sample or material.

In the illustrated examples, the material pathways represent examples of transport paths that may be traveled by a physical sample in a laboratory or hospital. A typical progression of the material from one station to the next is depicted by the direction of the arrow. However, it should be understood that the processing stations are provided as examples, as are the directions of material flow. It shall be appreciated that more, fewer or other processing stations may be used in practice of the present invention, and/or more, fewer or other material paths and directions may be used in the practice of the present invention.

Any form of transport may be used that is sufficient to transport the material as indicated by the material pathways. For example, material may be robotically transported from one station to the next. It may also, or alternatively, be hand carried from one station to the next. Additionally, one machine may perform multiple steps with no physical movement of the material from one station to another being required.

Figure 2:
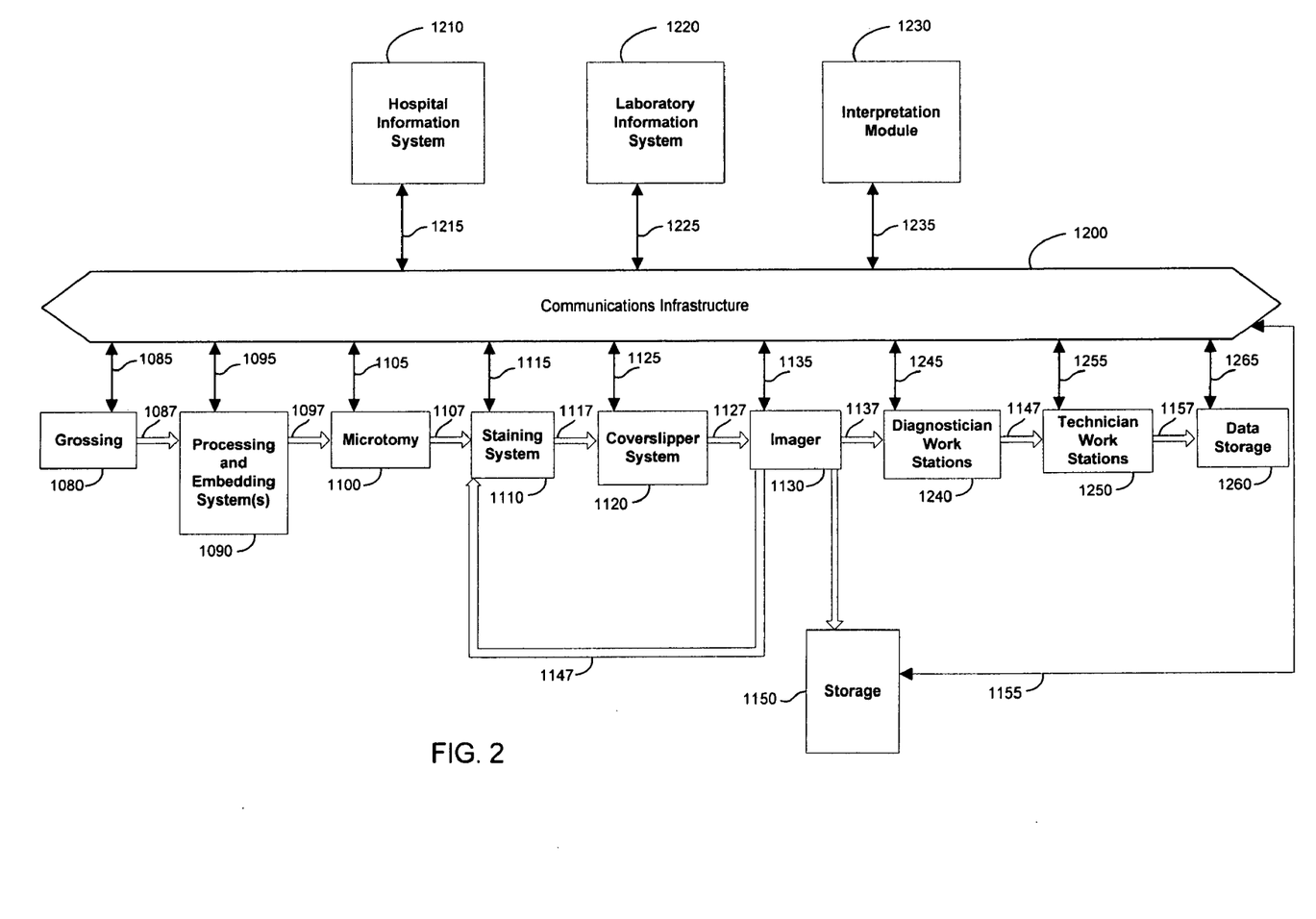
FIG. 2 is a block diagram of an example of an automated system for processing and examining biological specimens in accordance with the present invention.

In the embodiment of FIG. 2, a grossing station 1080 is provided in which a tissue grossing operation may be performed. Of course, it should be appreciated that grossing is not always a requirement, especially in the case of processing biological fluids. After the grossing station, a sample in the illustrated example may travel on material path 1087 to a processing and embedding station 1090.

The processing and embedding station may include manual or automated processing leading to a paraffin infiltrated and embedded sample. It should be appreciated that processing and embedding system 1090 may include multiple pieces of automated processing equipment, or it may include a combination of one or more pieces of automated processing equipment with manual processes. In one example, an automated tissue processor is used at the processing and embedding station 1090. In another embodiment an automated embedding instrument is used. In another embodiment, these instruments are at two different locations and there is a material pathway (not shown) between them. Alternatively, they may be incorporated in a single instrument, or can be in two instruments with automated transport between. The same is true of all the processing stations discussed herein, namely that they can be combined and automated as desired. This reflects the flexibility of the present system in that it is adaptable to any of the numerous automated solutions available, under development, or conceivably developed in the future.

Following processing and embedding system 1090 the material may be transported along path 1097 to a microtome station 1100, also referred to as "microtomy". Material sections, or slices, are created in microtome station 1100, although it should be understood that any technology of creating sections thin enough for microscopic examination may be used. It should be appreciated that if thin material sections are not needed for examination microtomy would not be necessary.

In a typical practice of the invention, sections created in microtome station 1100 are positioned on microscope slides. Following microtomy 1100, the biological tissue sections (and slides) may move along pathway 1107 to a staining system 1110. Any staining or other test protocol may be performed as desired. In a preferred embodiment, an automated stainer is used. In an example, staining with hematoxylin and eosin ("H & E") is performed in an staining system 1110. Following staining, the samples may be transported along material path 1117 to a coverslipper system 1120 to be coverslipped. It should be appreciated that coverslipping and staining are both optional and, if included, may be performed manually or automatically.

In the embodiment shown in FIG. 2, staining system 1110 is located before coverslipper system 1120 along the material path, however this ordering is not required, and the steps associated with those systems could be performed in other orders. In one particularly desirable example, coverslipper system 1120 is located before staining system 1110. In this example, a coverslip may be applied to a microscope slide and then the covered slide may be transported to staining system 1110. After staining the slide may proceed to an imager 1130.

In an embodiment, the coverslipper and staining systems are automated and combined in a single automated device. In another alternative, a coverslipper system is not required. In still another embodiment, the coverslipper system 1120 is located downstream of the imager 1130 in the material path. It therefore should be understood that if a coverslip is applied, that application may occur at any desired location, either before or after imaging and before or after staining. Generally speaking, following coverslipper system 1120, the pre-examination processing is complete, and the tissue sample(s) are ready for the examination processing.

As the material proceeds along the material pathways and through the processing systems, information may be shared between the numerous devices using various information pathways that form a communications infrastructure 1200. It should be noted that communications infrastructure 1200 may be any form of communication system enabling communications between and amongst individuals, computer systems and/or automated processing systems. In an example, the communications infrastructure may be a computer network that is wired, wireless or a combination of wired and wireless. For example, information access points may be wired into the network and/or joined to the network via a wireless portal. Although the illustrated example shows a networked system in which communications are performed via a network, direct communications also may be conducted. For example in one embodiment, processing and embedding system 1090 may have a direct communications link with staining system 1110 and may access the communications network via a node in staining system 1110, or alternatively it may have a direct network link. It should be understood that any suitable communications pathway structure is envisioned which would enable suitable sharing of information between and amongst various system components. Likewise, it should be understood that, in other embodiments, not all of the system components may have a direct communications path. Furthermore, it should be understood that the communication pathways can take any form, such as digital, analog, wired, wireless, paper, oral, telephonic, etc.

In an embodiment, a laboratory network may be provided as the portion of the communications infrastructure 1200 between and amongst the laboratory instruments, depicted with reference numbers 1080, 1090, 1100, 1110, 1120, 1130, 1140, 1230, and also the laboratory information system 1220 and other work stations 1240 and 1245 (which might include a computer system such as for example one or more personal computers and/or computer servers). The laboratory network may be networked with a hospital network that is also a part of the communications infrastructure 1200. In such an embodiment, other devices may have access to the information available on the laboratory information system 1220 or other laboratory devices via the communications infrastructure 1200. Such other devices include for example, diagnostician or administrator work stations 1240, a hospital information system 1210, and in some embodiments the interpretation module 1230 as well. It should be understood that the flexibility of the information pathways is directed to enable the necessary information flow to track biological samples being processed however desired, and to distribute the necessary information to the appropriate users. Numerous alternative communications system structures may be selected to meet this need, and the illustrated and discussed examples are provided for illustrative purposes only, not to limit the scope or flexibility of the system.

Referring to the illustrated example, information pathway 1085 represents an example of a communications pathways between the grossing station 1080 and any other desired component via communications infrastructure 1200. Likewise, communications pathways 1095, 1105, 1115, 1125, 1135, 1155, 1215, 1225, 1235, 1245, 1255 and 1265 represent examples of communications pathways between processing and embedding stations 1090, microtomy 1100, staining system 1110, coverslipper system 1120, imager 1130, storage facility 1150, hospital information system 1210, laboratory information system 1220, interpretation module 1230, diagnostician work station 1240, technician work station 1250, and/or local or remote data storage 1260, or any other desired component.

The sharing of information may be automated, manual or conceptual. For example, information may be shared directly by two machines in communication with each other, it may be made available to a user who can manually input it into another device, or a single machine comprising more than one device shown in FIG. 2 can engage in internal communication. This sharing of information often involves two-way communication. For example, images from a patient having a chronic condition may be sent to a database of patient information storage, and previously obtained information regarding the same patient may be retrieved from the database in order to monitor the progression of the condition. In another embodiment, each station in the material path is capable of communicating via the communications infrastructure 1200 and the stations may communicate the progression of the material along the material pathways as well as other information, as discussed in further detail below.

In another embodiment of the invention, biological specimens, containers, workpieces, and locations throughout the system may be identified with machine understandable codes, such as provided by RFID tags, shape identifiers, color identifiers, numbers or words, other optical codes, barcodes etc. The identifiers can be recorded to generate data provided to a database, such as data maintained in data storage device 1260, by a PC (any computing devices), hospital information system 1210, laboratory information system 1220 or any combination thereof. Examples of data that may be tracked include patient information and history, information regarding biological sample(s) collected, arrival and departure times of biological samples, tests performed on the samples, processes performed on the samples, reagents applied to the samples, diagnoses made, associated images and so on.

The next step performed by the automated system for processing and examining biological specimens is examining the specimen. In that step, the biological sample is received by imager 1130 after being processed for imaging as desired. In the example illustrated in FIG. 2, the processing is sufficient once the desired staining has been completed, such as in staining system 1110, and optionally a microscope slide has been applied (either before or after staining) in coverslipper system 1120. At least one image of the material specimen is obtained by imager 1130. Imager 1130 may include one or more imagers. The imager can be any system that generates images that can be interpreted in interpretation module 1230. In the illustrated embodiment, imager 1130 includes a microscope and a camera capable of recording digital images of the microscope's view field. For example an optical CCD based camera can be used to generate the digital image data. The digital image data can be stored in any fashion that provides for access to the data as required by the interpretation module 1230, diagnostician work station 1240 and/or technician work station and/or as desired by anyone needing access to the image data, such as diagnosticians or laboratory personnel. Examples of suitable data storage are local storage device associated with the imager 1130 (such as hard drive, removable memory, flash memory, optical memory such as CD or DVD etc.), and/or networked memory such as diagrammatically illustrated by data storage 1260. It should be noted that any form of information may be generated by the imager 1130, in addition to the image data. For example the imager 1130 may optionally associates other types of data, such as a log of patient information associated with the image data and as discussed further herein. Alternatively, another processing system may associate the image data with other data.

The type of information generated is intended to be sufficient for the interpretation module 1230 to perform its interpretation processing and generate the desired report. The interpretation module 1230 may take any desired form, such as for example, a dedicated computing system, or alternatively it may be a module running on a computing system used for multiple purposes. In additional examples, it may be free-standing, a part of the imager 1130, part of the hospital information system 1210, part of the laboratory information system 1220, or it may be in any location where data may be received from the imager 1130. Although the figures depict a single interpretation module 1230, it should be understood that plural interpretation modules 1230 also may be used. In further examples, diagnostician work stations 1245 may include interpretation modules 1230 or interpretation module clients that enable the diagnostician to locally conduct an interpretation based on the data available including, without limitation, image data from the imager 1130.

In the embodiment of FIG. 2, the interpretation module(s) 1230 is in communication via the communications infrastructure 1200. Interpretation module 1230 may access data as desired, whether directly from the imager 1130, via data storage facility 1260, or via local data storage. Interpretation module uses the image data and other data to perform an analysis and a recommendation. In an embodiment, the analysis includes a pattern recognition analysis in a pattern recognition system of the interpretation module 1230. In one form of pattern recognition, image data from the imager 1130 is compared to a database of known patterns. If a sufficient level of correspondence is found, a matching pattern is located upon which a recommendation, diagnosis or further processing instruction can be made. The pattern database can be a part of the interpretation module 1230, or located externally, such as for example in data storage 1260 or laboratory information system 1220.

Following imaging in the imager 1130, the further processing of the imaged sample may be routed either as directed by a technician, diagnostician or other person, or preferably as automatically indicated by the interpretation module 1230. The interpretation module 1230 for example is configured to determine whether the particular sample needs to undergo additional processing, in which case it may proceed along material pathway 1147, or alternatively that it should go to a storage facility 1150, in which case it proceeds along material pathway 1157, or alternatively that it should go to a diagnostician or other personnel for personal inspection, in which case it proceeds along material pathway 1247. In the illustrated example, where the sample proceeds for additional processing, sample is returned to stainer 1110 via pathway 1147 where it may undergo other operations such as special staining, immunohistochemistry ("IHC"), in situ hybridization ("ISH"), multiplexing or other staining or testing procedures. Subsequently, the sample may proceed along the material path as already discussed, for example, back to the imager 1130. Ultimately it is desired that the tested and imaged sample be stored as indicated by storage 1150. In this example, after personal inspection by a diagnostician or other person, the sample may be returned for further processing, such as to staining system 1110 or for storage, such as in storage facility 1150. Later, the processed sample can optionally be retrieved from the storage facility 1150 if desired.

Figure 3:
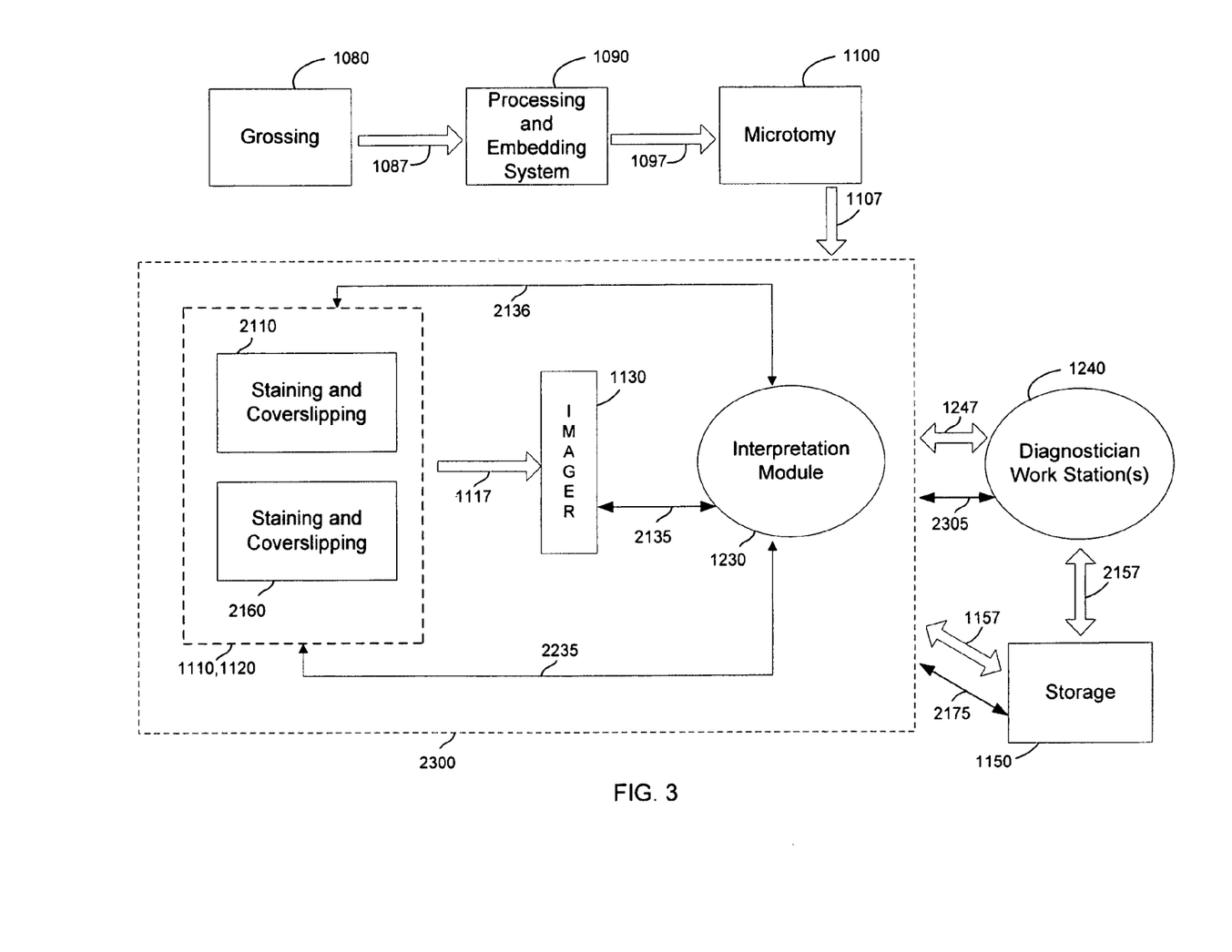
FIG. 3 is a block diagram of another example of an automated system for processing and examining biological specimens in accordance with the present invention.
Figure 4:
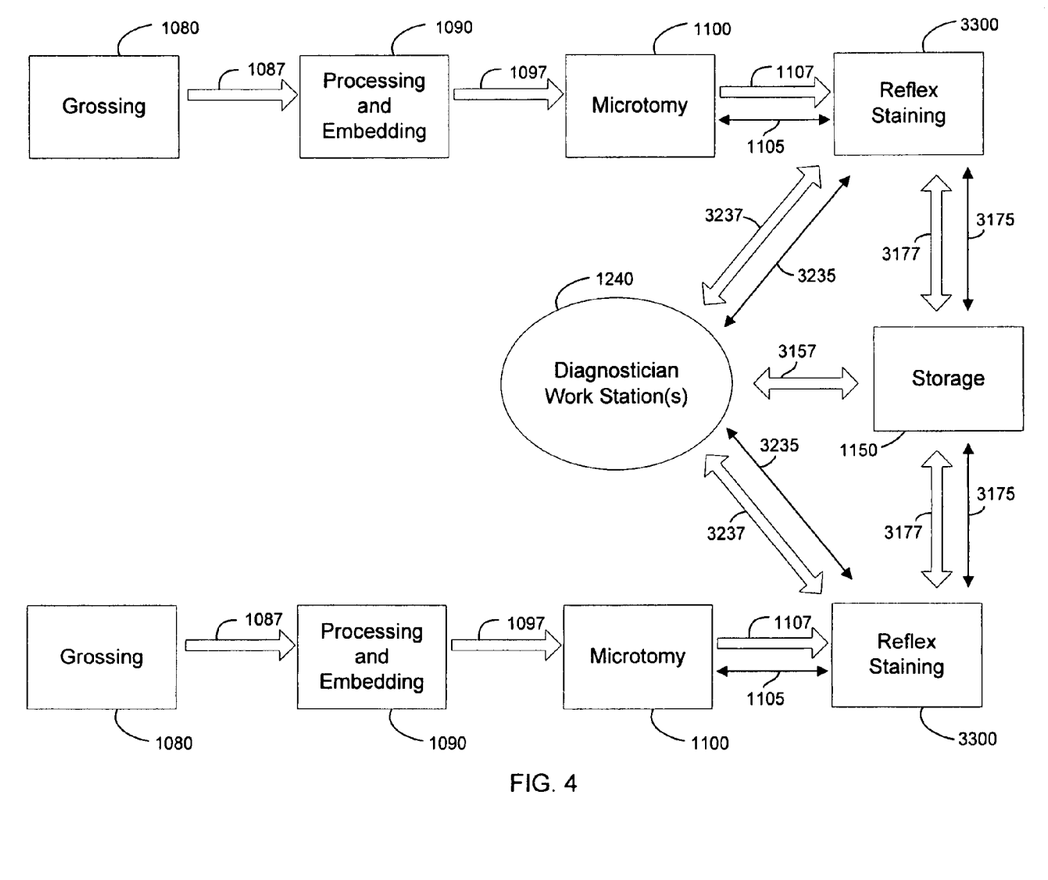
FIG. 4 is a block diagram of another example of an automated system for processing and examining biological specimens in accordance with the present invention.
Figure 5:
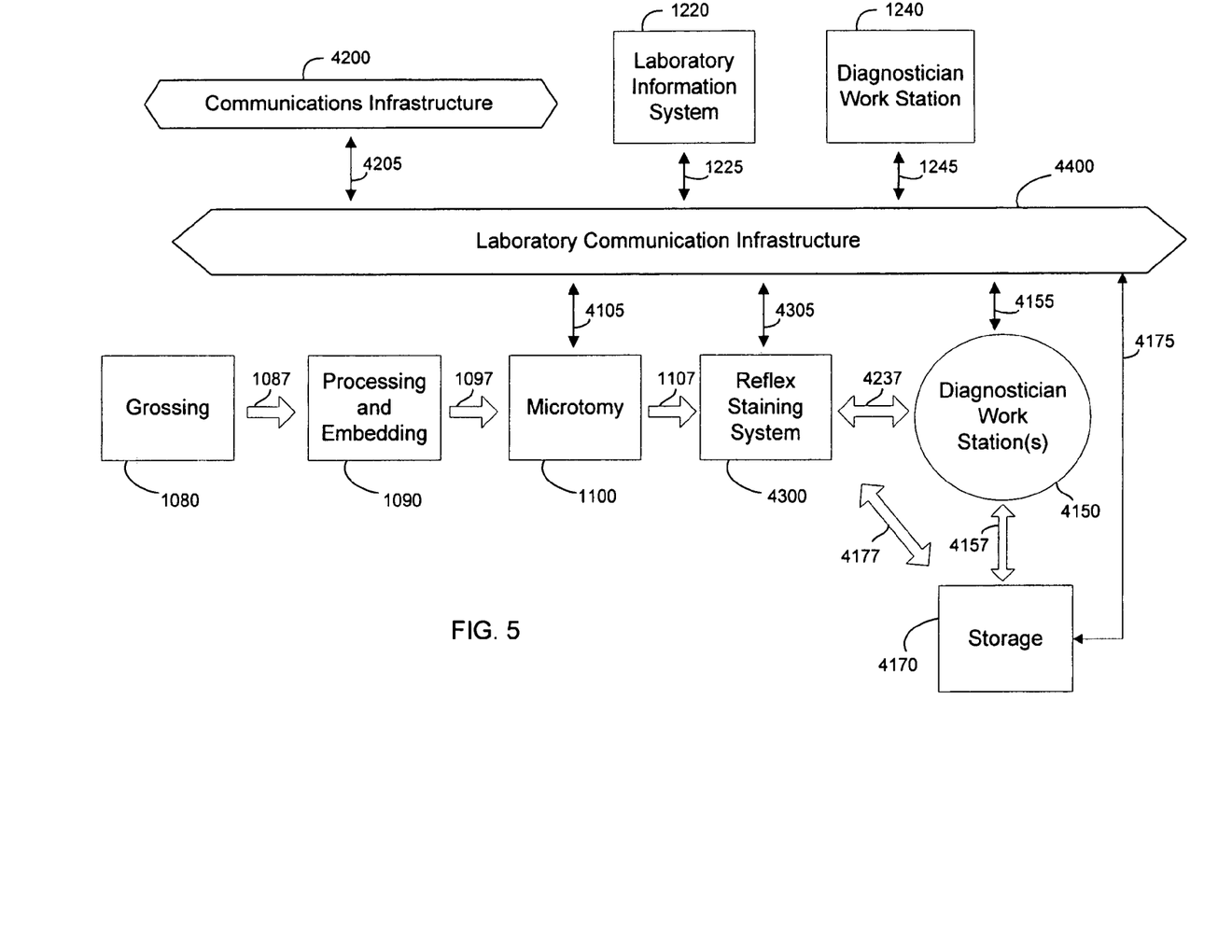
FIG. 5 is a block diagram of another example of an automated system for processing and examining biological specimens in accordance with the present invention.

The work stations, such as diagnostician work stations 1240 or other work stations, such as technician work stations 1250 can have any desired structure, including computing systems in communication via the communications infrastructure 1200 with other components of the system. The work stations may optionally also include other components that might be useful in a work area, such as material storage units, furniture, phones etc. In an embodiment, the work stations 1240, 1250 provide access to information concerning the processing of biological samples, and the results of the processing, including image data from the imager 1130 and interpretation data or reports from the interpretation module 1230. Other examples of systems for processing biological specimens are illustrated in FIGS. 3, 4 and 5. FIG. 3 illustrates an embodiment in which a reflex staining module 2300 includes staining system 1110, imager 1130 and interpretation module 1230, which are grouped together and implemented as a single automated instrument, a reflex staining module 2300. Alternatively, they may be in separate instruments at different locations. The pre-examination processing may be performed by instruments both inside and outside the reflex staining module 2300, such as for example in grossing 1080, processing and embedding system 1090, microtomy 1100 and staining and coverslipping systems 1110, 1120. As already discussed, it should be understood that coverslipping and staining can be located in any desired order or alternatively in a single instrument. Two staining systems are illustrated as a part of the staining system 1110 in this embodiment In particular, staining system 1110 includes H&E/SS staining and coverslipping 2110 and IHC/ISH staining and coverslipping 2160. At H&E/SS staining and coverslipping 2110, the biological sample may undergo H & E or special stain ("SS") staining and optional coverslipping. At IHC/ISH Staining & Coverslipping 2160, the material may undergo immunohistochemistry ("IHC") or in situ hybridization ("ISH") staining, and a coverslip may optionally be applied to the slide. Other staining or testing protocols also can be performed. Following the stainer/coverslipper 1110,1120, the biological sample proceeds along material pathway 1117 to the imager 1130 within the reflex staining module 2300. It should be understood that the material pathway 1117 is optional and the sample may remain stationary or may move to an intermediate location, at which image data is created by imager 1130.

In the illustrated example, the image data proceeds along data path 2135 to interpretation module 1230, located in the reflex staining unit 2300. Although a direct data path is indicated, it should be understood that communication by any of the apparatus discussed previously, including networks, may be used to provide data to the interpretation module 1230, or to provide an access location at which the interpretation module 1230 can access data, such as a local or remote data storage module 1260. Although communications infrastructure 1200 is not illustrated in FIG. 3, it should be understood that the various components have data pathways to a communications infrastructure 1200 or alternatively between and amongst one another. In this example there is depicted an information pathway 2305 between the diagnostician work station 1240 and the reflex staining module 2300 and an information pathway 2175 between a storage facility 1150 and the reflex staining module 2300. It should be understood that these can be direct information pathways as illustrated or alternatively indirect pathways via a communications infrastructure 1200 not shown in FIG. 3. Subsequent processing of the biological sample also can be performed as indicated by the interpretation module 1230 diagnostician or other person, in the iterative processing discussed previously. FIG. 3 also depicts a material pathway between the diagnostician work stations 1240 and storage 1150.

FIG. 4 depicts another alternative embodiment of a material and information handling apparatus in which the present invention may be implemented. Similar to the previously described embodiments, thin solid arrows are used to denote pathways of information, as defined above, such as information path 3105, information path 3175, and information path 3235. In addition, thicker hollow arrows are used to denote material pathways, as defined above, such as material path 3087, material path 3097, material path 3107, material path 3177, material path 3157, and material path 3237.

The embodiment shown in FIG. 4 has many similarities to the embodiment shown in FIG. 3. Briefly, material proceeds from grossing 1080 to processing and embedding 1090 to microtomy 1100 and then to reflex staining 3300. From Reflex Staining, the material may be sent to diagnostician work station 1240 or storage 1150, and between those two stations. Each of those stations has the same description and material and information sharing characteristics as the corresponding station discussed above in relation to FIG. 3.

The system illustrated in FIG. 4 demonstrates that multiple tissue collection and pre-examination processing systems may be combined in a larger system. Thus, in a single laboratory, multiple grossing stations 1080, processing and embedding stations 1090 and/or microtomy 1100 may exist. Likewise, more than one reflex staining modules 3300 station may exist, all of which may be in communication with the pathologist through diagnostician work station 1240. In a preferred embodiment, the system shown in FIG. 4 is largely automated, providing a highly efficient laboratory without any significant increase in manpower.

Referring now to FIG. 5, another alternative embodiment of a material and information handling system is depicted in which the present invention may be implemented. Thin solid arrows are used to denote pathways of information, as defined above, which include information path 4105, information path 4155, information path 4175, information path 4205, information path 1225, information path 1245, and information path 4305. Thicker hollow arrows are used to denote material pathways, as defined above, which include material path 1087, material path 1097, material path 1107, material path 4157, material path 4177, and material path 4237.

Briefly, material proceeds from grossing 1080 to processing and embedding 1090 to microtomy 1100 and then to reflex staining system 4300. From reflex staining system 4300, the material may be sent back and forth between diagnostician review 4150 and/or storage 4170, and also between each of those two stations. Each of these stations has the same description and material sharing characteristics as the corresponding station discussed above in relation to the embodiment of FIG. 3.

The embodiment shown in FIG. 5 includes laboratory communication infrastructure 4400, which allows information to be communicated between two or more stations. As shown here, this communication may occur between microtomy 1100, reflex staining system 4300, diagnostician workstation 4150 located within the material path, diagnostician work station 1240 located outside the material path, storage 4170, laboratory information system 1220, and communications infrastructure 4200.

Communication infrastructure 4200 provides communication of information to other locations in the hospital and may provide communication of information to external locations, such as universities, other hospitals, remote facilities, and the internet. It should be understood that communication path 4205 between laboratory communication infrastructure 4400 and communication infrastructure 4200 is optional. If communication path 4205 is removed, the material and information handling apparatus embodiment shown in FIG. 5 becomes a closed system and may still operate to evaluate material samples and to provide findings based on the self-contained databases, such as in laboratory information system 1220 or any database within reflex staining system 4300 or any other station in communication with the laboratory communication infrastructure 4400. Hence, removal of information path 4205 results in a stand-alone laboratory material and information handling system.

Figure 6:
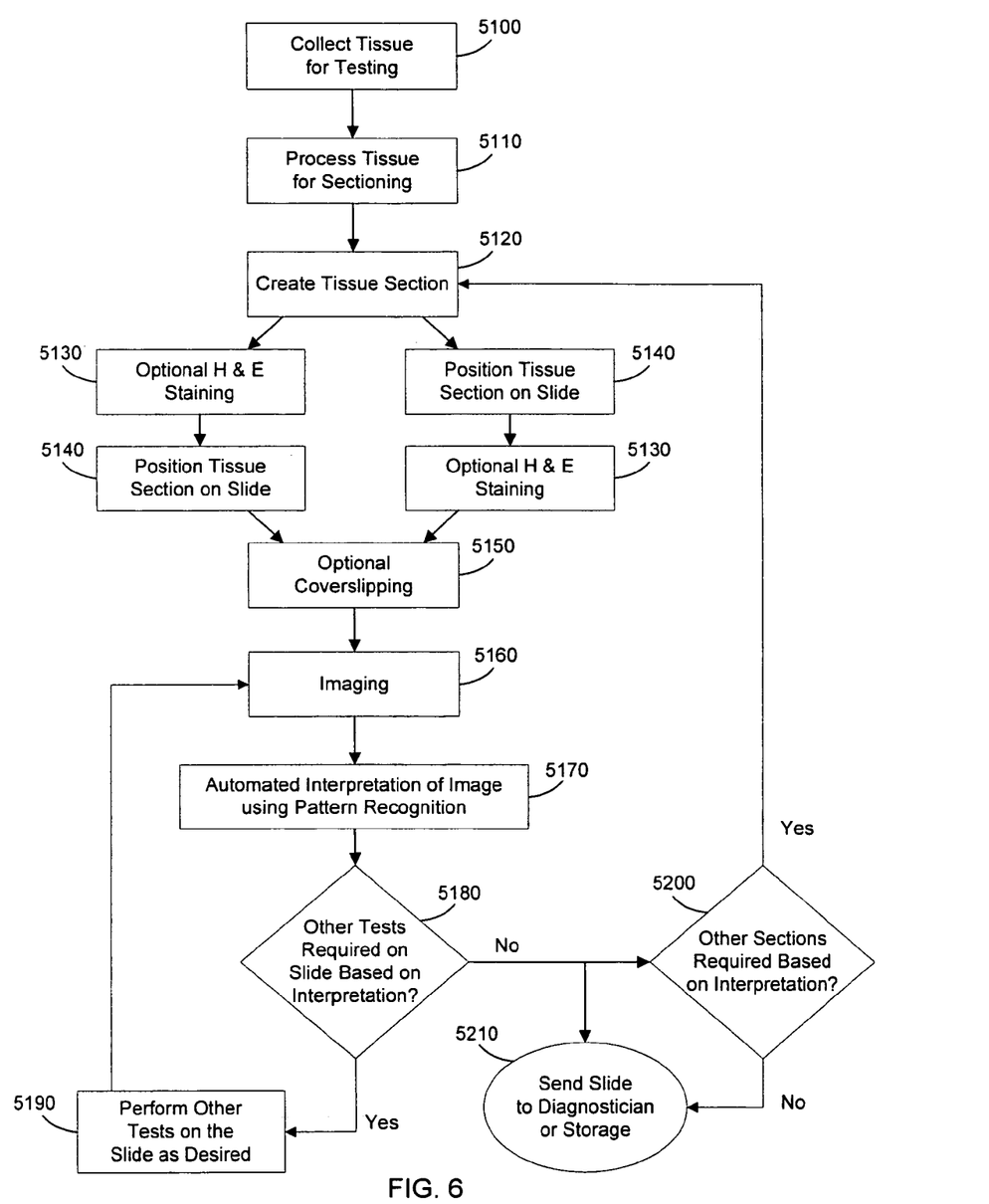
FIG. 6 is a flow chart illustrating an example of processing steps performed by an automated system for processing and examining biological specimens in accordance with the present invention.

In FIG. 6, a method of processing and examining a biological specimen in an automated system is shown. First, in step 5100 a specimen, such as a tissue sample, is collected for testing. This step may involve collecting a sample such as by biopsy or drawing a fluid from a patient or otherwise excising a sample from a patient. Next, step 5110 requires that the sample be processed for sectioning. The processing step may require that the material undergo procedures, such as freezing or paraffin-embedding.

Next, a section is created, such as with a microtome or other sectioning device, as shown in step 5120. Once sectioned, the material is then placed on the slide, and may undergo H & E staining, as shown by steps 5130 and 5140. Two pathways are shown with these steps to illustrate the optional order these steps may be performed. Following these procedures, a coverslip optionally may be placed on the slide in the optional coverslipping step 5150.

Imaging 5160 is the next step shown in the flow chart of FIG. 6. In this step, one or more imagers are preferably used to obtain one or more images of the material that can be compared to other images or information. In a preferred embodiment, a stained slide is positioned under a microscope and at least one digital color image is created. In the next step, the image is interpreted using pattern recognition as shown in step 5170, which involves the use of automated pattern recognition technology to interpret the image and provide an initial assessment of the material. In a preferred embodiment, an interpretation module (not shown) would be used to accomplish this step, as discussed below. Based on the results of the interpretation, the next step, step 5180, queries whether the particular material that was imaged should undergo further testing or staining. Preferably, this step determines whether the interpretation results include any unidentified abnormalities. If so, and if the system determines that additional staining or tests on the slides may help identify the abnormality, then the slide undergoes the additional staining or tests as indicated by step 5190. Next, the slide is sent back to the imaging step 5160 where the process may be repeated.

After the interpretation has identified the material as normal, abnormal with a recognized abnormality, or abnormal with an unrecognized abnormality requiring no additional testing, the decision from Other Tests Required on Slide Based on Interpretation? step 5180 results in a "no" response. Once a "no" result occurs, the material and slide can be sent to the diagnostician or stored in the end step Send Slide to Pathologist or Storage 5210, discussed in more detail below. Additionally, a "no" result from Other Tests Required on Slide Based on Interpretation? 5180 step also advances the process to the next decision step, which determines if additional sections are required based on the interpretation, as shown in step 5200.

Step 5200 queries whether one or more additional slides should be prepared to undergo additional testing. This step is answered in the affirmative in the event that the material under consideration was found to be abnormal and further testing of other samples is desired. A "yes" response from step 5200 returns the process to the earlier step 5120 of creating a tissue section and the process is continued from that step. In another embodiment of this system, several sections of biological material initially may be prepared at step 5120. In that embodiment, an affirmative response from the Other Sections Required Based on Interpretation? step 5200 directs the staining of one of the already prepared slides.

Still referring to the Other Sections Required Based on Interpretation? step 5200 of FIG. 6, when no further testing is recommended on the material from which the section or sections have been imaged, a "no" response is generated and the material is either sent to the pathologist or to storage. This final step 5210 is to send the slide to a diagnostician or storage. In the event that multiple slides undergo imaging, a preferred system provides temporary storage of the individual slides until the process is complete, at which time all slides and information regarding the preliminary findings and determinations may be communicated to the diagnostician en masse.

In an alternate embodiment, each slide is sent to storage in the end step and the images, interpretations, and other information are sent to the diagnostician in a piecemeal fashion. For example, this embodiment may deliver information electronically to the diagnostician's computer so that the diagnostician has real-time access to information and the progression of the system operation. At the conclusion of all imaging and evaluation of the biological material, a message can be communicated to the diagnostician advising of the completion of the process.

Once the pathologist or other diagnostician has reviewed any or all of the information communicated by the process shown in FIG. 6, that person may recommend further testing on the material previously studied or request that further material be collected, processed, or sectioned in order to undergo additional testing. Under these circumstances, the diagnostician can initiate the process from the appropriate step of the flow chart.

The flow chart shown in FIG. 6 may be modified with the addition of pre-defined staining protocols that produce a number of slides and are based on the organ or pre-identified medical condition. For example, the laboratory may choose to routinely perform a panel of three stains on breast tissue samples, such that all slides will be imaged and interpreted prior to the review by the pathologist or diagnostician.

Figure 7:
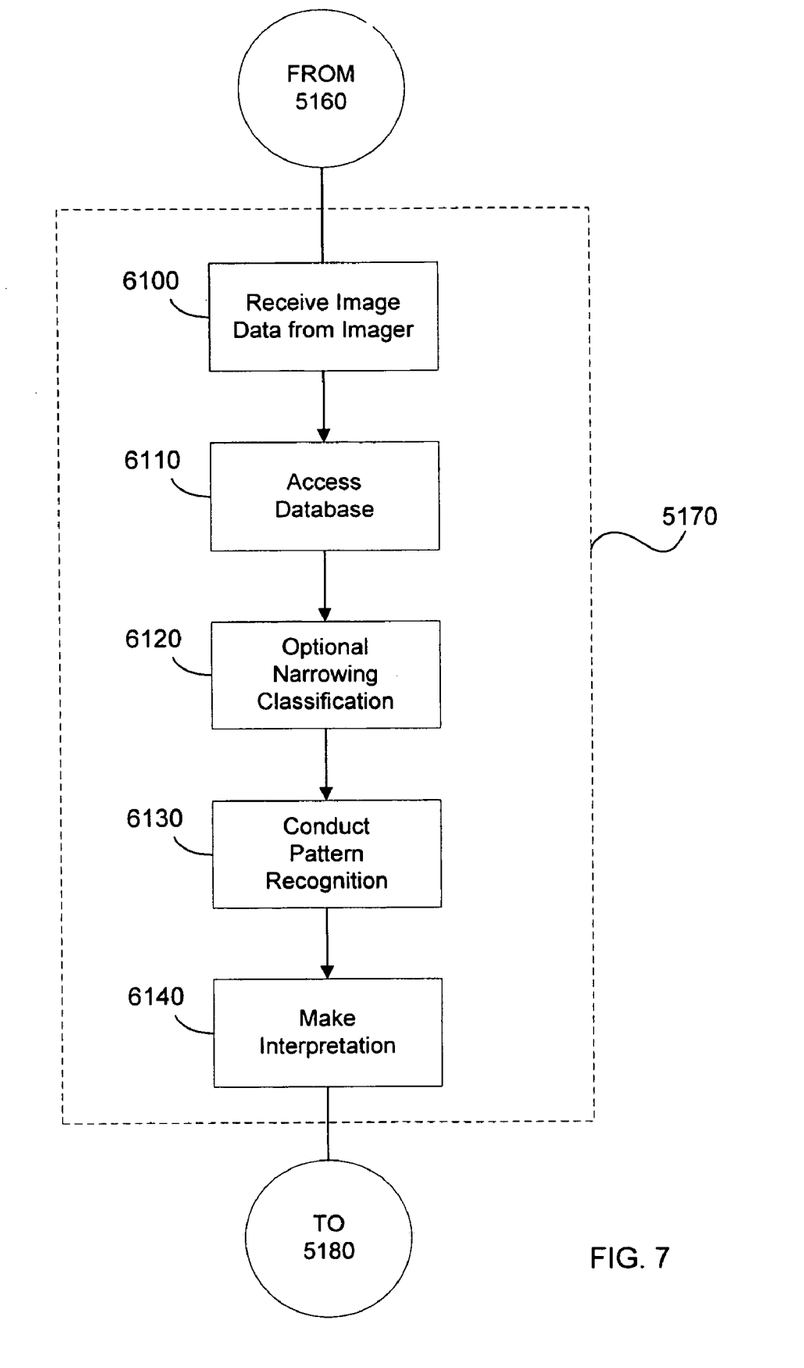
FIG. 7 is a flow chart illustrating an example of processing steps performed by an automated system of processing and examining biological specimens in accordance with the present invention.

FIG. 7 depicts an example of a method for interpreting image data by an interpretation module (not shown), and specifically as used in accordance with step 5170 of the embodiment of the present invention shown in FIG. 6. As in FIG. 6, the arrows in FIG. 7 represent advancement from one step to the next, as opposed to specific movement of material or information.

The interpretation module system begins with the receipt of image information from imaging step 5160, as shown in step 6100. Preferably, this image data information is automatically transferred between the devices.

After the interpretation module receives the image data, it may gather information from one or more available databases in access database step 6110. The databases may be included in a hospital information system, a laboratory information system, and/or a patient database, such as those discussed above.

Information from the databases may be filtered or screened as desired in the optional narrowing classification step 6120. In this step, criteria may be utilized to focus the database information to specific data, or alternatively to exclude certain data from the database information. For example, information regarding tissue type may be used to confine the communications to information concerning tissue of the same type of material. As another example, the communicated information may focus on images taken of prior samples from the same patient in order to facilitate tracking the progression of that person's particular condition.

Once the interpretation module has access to the database and any optional narrowing criteria has been applied, it may proceed to the conduct pattern recognition step 6130, in that step, the image data of the sample is compared known information from the database or databases. After the comparison is made, the next step 6140 requires an interpretation in which the interpretation module may provide a preliminary finding based on the comparisons made during the pattern recognition. The system may optionally repeat the method by returning to the access database step 6100 one or more times before proceeding.

In a preferred embodiment, the interpretation step 6140 also generates information relating to whether additional tests or staining should be conducted on the already tested samples and/or whether additional samples should be tested. The information generated can assist a diagnostician or the system in making decisions later in the flow chart shown in FIG. 6. The generated information may include, for example, the types of additional tests or procedures that should be performed. In any event, the interpretation module preferably communicates its assessments, preliminary findings, recommendations, and other information to the communications infrastructure, laboratory communications infrastructure, or other appropriate components, as discussed above. Following the interpretation of the pattern recognition data, the next step requires the sample to be advanced to the step of determining whether additional tests are required, shown as step 5180 in FIG. 6.

Thus, a slide management and interpretation system and method are provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A system of processing biological specimens, comprising:
   a biological material handling system;
   a communication infrastructure in communication with the material handling system;

a slide processing module including at least one of a staining module and a testing module;

a slide imaging module in communication with the communication infrastructure and generating slide image data; and an interpretation module in communication with the slide imaging module utilizing pattern recognition technology to compare the slide image data to reference image data in order to generate an initial interpretation of the image data, the interpretation module communicating with the material handling system and the slide processing module to return the slide to the slide processing module and obtain additional staining or testing in accordance with the initial interpretation of the image data, wherein the staining module, the slide imaging module and the interpretation module are implemented as a single automated instrument.

2. The system of processing biological specimens of claim 1, further comprising a determination module generating staining instruction data for carrying out at least one staining procedure in the staining module in accordance with said staining instruction data.

3. The system of processing biological specimens of claim 2, further comprising: a sectioning device; and a sectioning instruction receiving module.

4. The system of processing biological specimens of claim 3, further comprising a coverslipper module.

5. The system of processing biological specimens of claim 1 wherein the interpretation module is in communication with the slide imaging module via the communications infrastructure.

6. The system of processing biological specimens of claim 1 wherein the interpretation module is in communication with the slide imaging module via a direct data path.

7. A system of processing biological specimens, comprising:

a biological material handling system;

a communication infrastructure in communication with the material handling system; a slide preparation module;

a slide imaging module in communication with the communication infrastructure and generating slide image data for a slide under test; and an interpretation module in communication with the slide imaging module utilizing pattern recognition technology to compare the slide image data to reference image data in order to generate an initial interpretation of the image data, the interpretation module communicating with the material handling system and the slide preparation module to prepare and image an additional slide in response to the initial interpretation of the image data, wherein the staining module, the slide imaging module and the interpretation module are implemented as a single automated instrument.

8. The system of processing biological specimens of claim 7, further comprising a determination module generating staining instruction data for carrying out at least one staining procedure in the staining module in accordance with said staining instruction data.

9. The system of processing biological specimens of claim 8, further comprising: a sectioning device; and a sectioning instruction receiving module.

10. The system of processing biological specimens of claim 9, further comprising a coverslipper module.

11. The system of processing biological specimens of claim 7 wherein the interpretation module is in communication with the slide imaging module via the communications infrastructure.

12. The system of processing biological specimens of claim 7 wherein the interpretation module is in communication with the slide imaging module via a direct data path.

13. The system of processing biological specimens of claim 7 wherein the additional slide is at least partially prepared concurrently with the slide under test.

* * * * *